US010925983B2

(12) United States Patent
Dayton

(10) Patent No.: US 10,925,983 B2
(45) Date of Patent: Feb. 23, 2021

(54) DECONTAMINATION METHOD AND APPARATUS

(71) Applicant: Diversey, Inc., Fort Mill, SC (US)

(72) Inventor: Roderick M. Dayton, Strongsville, OH (US)

(73) Assignee: Diversey, Inc., Fort Mill, SC (US)

( * ) Notice: Subject to any disclaimer, the term of this patent is extended or adjusted under 35 U.S.C. 154(b) by 0 days.

(21) Appl. No.: 16/518,053

(22) Filed: Jul. 22, 2019

(65) Prior Publication Data

US 2019/0336630 A1 Nov. 7, 2019

Related U.S. Application Data

(63) Continuation of application No. 15/205,716, filed on Jul. 8, 2016, now Pat. No. 10,357,583, which is a
(Continued)

(51) Int. Cl.
*A61L 2/10* (2006.01)

(52) U.S. Cl.
CPC ........... *A61L 2/10* (2013.01); *A61L 2202/122* (2013.01); *A61L 2202/14* (2013.01);
(Continued)

(58) Field of Classification Search
CPC ........ A61L 2/08; A61L 2/10; A61L 2202/122; A61L 2202/14; A61L 2202/16; A61L 2202/182; A61L 2202/24
See application file for complete search history.

(56) References Cited

U.S. PATENT DOCUMENTS 2,608,487 A * 8/1952 Kauffman ............... A22C 17/14
426/234
4,469,951 A * 9/1984 Coco .................... A61N 5/0614
250/454.11
(Continued)

OTHER PUBLICATIONS

U.S. Appl. No. 15/205,716, Non-Final Office Action, dated Jun. 26, 2018, 17 pages.
(Continued)

*Primary Examiner* — David E Smith
(74) *Attorney, Agent, or Firm* — Kilpatrick Townsend & Stockton LLP

(57) ABSTRACT

Provided is an apparatus for disinfecting objects of various shapes and sizes. The apparatus includes a housing enclosing a disinfecting chamber, and an ultraviolet light source arranged to emit ultraviolet light into the disinfecting chamber to deactivate at least a portion of a biologically-active contagion present on the object. A peripheral wall of the housing that extends about a portion of the disinfecting chamber comprises an ultraviolet-reflective material so that the ultraviolet light impinging on the peripheral wall is reflected generally away from the peripheral wall and toward an interior of the disinfecting chamber. A door is adjustable between open and closed orientations. A floor at the bottom of the disinfecting chamber includes an ultraviolet-reflective surface that reflects the ultraviolet light impinging on the floor generally away from the floor toward the interior of the disinfecting chamber.

20 Claims, 7 Drawing Sheets

Related U.S. Application Data continuation of application No. PCT/US2015/027976, filed on Apr. 28, 2015.

(60) Provisional application No. 61/985,246, filed on Apr. 28, 2014.

(52) U.S. Cl.
CPC ..... *A61L 2202/16* (2013.01); *A61L 2202/182* (2013.01); *A61L 2202/24* (2013.01)

(56) References Cited

U.S. PATENT DOCUMENTS

| | | | | |
|---|---|---|---|---|
| 6,165,526 | A * | 12/2000 | Newman | A23L 3/0055 422/24 |
| 6,504,898 | B1 * | 1/2003 | Kotler | G21K 5/04 378/64 |
| 7,781,745 | B2 * | 8/2010 | Rogers | A23L 3/263 250/455.11 |
| 8,143,596 | B2 * | 3/2012 | Yerby | A61L 2/10 250/455.11 |
| 10,357,583 | B2 * | 7/2019 | Dayton | A61L 2/10 |
| 2007/0075006 | A1 | 4/2007 | Watanabe et al. | |
| 2008/0067417 | A1 * | 3/2008 | Lane | A61L 2/24 250/455.11 |
| 2008/0067418 | A1 | 3/2008 | Ross | |
| 2009/0032527 | A1 * | 2/2009 | Lee | A23L 3/28 219/679 |
| 2009/0189085 | A1 | 7/2009 | Rogers | |
| 2009/0218512 | A1 | 9/2009 | Ranta et al. | |
| 2010/0044582 | A1 * | 2/2010 | Cooper | A61L 2/24 250/455.11 |
| 2010/0108917 | A1 * | 5/2010 | Stanley | A61L 2/10 250/504 R |
| 2012/0315184 | A1 | 12/2012 | Clark | |
| 2013/0078142 | A1 * | 3/2013 | Gordon | A61L 2/10 422/24 |
| 2014/0091044 | A1 * | 4/2014 | Jhawar | H05B 47/20 210/744 |
| 2014/0245866 | A1 | 9/2014 | Hadlock et al. | |
| 2014/0256866 | A1 | 9/2014 | Mcguire et al. | |
| 2016/0324997 | A1 | 11/2016 | Dayton | |

OTHER PUBLICATIONS

U.S. Appl. No. 15/205,716, Notice of Allowance, dated Mar. 11, 2019, 12 pages.

\* cited by examiner

DECONTAMINATION METHOD AND APPARATUS

CROSS-REFERENCE TO RELATED APPLICATIONS

This is a continuation of and claims priority to U.S. application Ser. No. 15/205,716, filed on Jul. 8, 2016, which is a continuation of International Patent Application No. PCT/US2015/027976, filed Apr. 28, 2015, which claims priority to U.S. Provisional Application No. 61/985,248, filed Apr. 28, 2014, the entirety of each of which is hereby incorporated by reference.

BACKGROUND OF THE INVENTION

1. Field of the Invention

This application relates generally to a method and apparatus for reducing contagions on an object and, more specifically, to a method and apparatus for suitably exposing an object to be used in a substantially-sterile environment to a disinfectant, which can optionally be a sterilizing agent.

2. Description of Related Art

Sterile, or at least substantially-sterile environments are common in the medical field for treating patients with minimal risk of infection. To avoid exposing patients in such environments to infectious organisms medical personnel working therein are required to take precautionary measures. All personnel are required to wash thoroughly before entering the environment, and wear items of clothing such as surgical scrubs that have been decontaminated.

Other objects such as medical equipment can also be contaminated with infectious organisms, and can pose a threat to introduce such organisms into the sterile environment. Bedding, medical devices, and virtually all other objects brought into a sterile environment must undergo sterilization procedures to minimize the risk of infection to patients. More recently, portable electronic devices such as tablet computers, for example, have become useful within sterile environments such as an operating room during a surgical procedure. Pulse oximeters, keyboards, and any other object that is often touched by hospital personnel or patients can also provide a means for transmitting infectious organisms when not properly and consistently decontaminated.

The wide array of electronic devices such as tablet computers and notebook computers, and medical devices, for example, that require decontamination pose additional problems when being considered for use in a medical environment. Their cases include apertures, seams, internal compartments and a variety of other structures where infectious organisms can hide from a liquid disinfectant or sterilizing agent, which is often topically applied as part of a decontamination process. Further, liquid disinfectants must be thoroughly applied, and remain wet long enough to achieve the desired level of decontamination, which makes the decontamination process time consuming, and unlikely to be correctly performed.

BRIEF SUMMARY OF THE INVENTION

Accordingly, there is a need in the art for a method and apparatus for sterilizing the variety of commonly used devices in the medical field regardless of the particular shape of the object.

According to one aspect, the subject application involves an apparatus for disinfecting objects of various shapes and sizes by placing the object in a housing enclosing a disinfecting chamber. The disinfecting chamber includes ultraviolet light sources that emit ultraviolet light to be imparted on the object in the disinfecting chamber for deactivating at least a portion of the biologically-active contaminant present on the object. The disinfecting chamber is lined with a reflective element so that the ultraviolet light may reflect around the chamber to provide maximum incidence with the object. The disinfecting chamber further includes a wall that is substantially-transparent to ultraviolet light so that objects may be leaned against it. A floor of the disinfecting chamber rotates during a disinfecting procedure to further provide maximum incidence between the object and ultraviolet light source. A no-touch door allows users to insert and remove objects to and from the disinfecting chamber without transferring biologically-active contaminants from their hands to the chamber. As the door rotates open, a shield similarly rotates to block ultraviolet light from the light sources while allowing access to the disinfecting chamber. Upon sensing that an object has been placed in the disinfecting chamber, the door rotates closed along with the shield, again exposing the disinfecting chamber to the ultraviolet light sources. Finally, a hook or hanging light source may extend downward from the upper surface of the disinfecting chamber to hang objects, particularly those with cords.

According to another aspect, the subject application involves an apparatus for rendering an object pathogen reduced. The apparatus includes a housing enclosing a disinfecting chamber in which the object is to be placed, and an ultraviolet light source arranged to emit ultraviolet light into the disinfecting chamber to be imparted on the object within the disinfecting chamber for deactivating at least a portion of a biologically-active contagion present on the object. A peripheral wall of the housing extends about a portion of the disinfecting chamber, and comprises an ultraviolet-reflective material so that the ultraviolet light impinging on the peripheral wall is reflected generally away from the peripheral wall and toward an interior of the disinfecting chamber. A door is adjustable between open and closed orientations to selectively permit access to the disinfecting chamber and interfere with emission of the ultraviolet light from the disinfection chamber into an ambient environment of the apparatus. A floor defines a bottom surface of the disinfecting chamber and comprising an ultraviolet-reflective surface that reflects the ultraviolet light impinging on the floor generally away from the floor toward the interior of the disinfecting chamber.

According to another aspect, the subject application involves a method for using the above-described apparatus for disinfecting commonly used devices and objects, particularly in the medical field.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
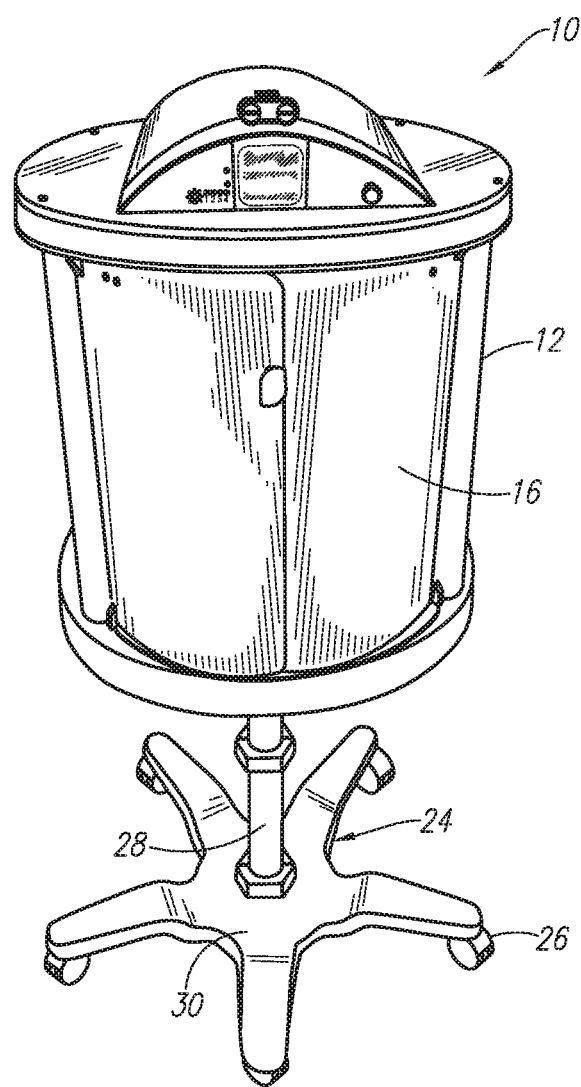
FIG. 1 is a perspective view of an illustrative embodiment of a decontamination apparatus, with a door closed during performance of a decontamination process.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

The disinfecting process performed by the present decontamination apparatus 10 and methods described herein can be performed on demand to render objects pathogen reduced, interchangeably referred to herein as materially-disinfected, as those objects are needed in an application, for example, a medical application. Rendering the object "pathogen reduced" does not necessarily require the object to be 100% sterile, free of any and all viable living organisms capable of reproduction to propagate an infection. Instead, to be "pathogen reduced" or "materially disinfected", the exterior surfaces of the object and the living contagions thereon must be exposed to ultraviolet-C ("UVC") light (e.g., having a wavelength of approximately 100 nm to approximately 280 nm) or other suitable disinfecting agent (e.g., radiation, etc.) for a suitable length of time to reduce the level of such viable contagions by a predetermined percentage for the particular application of the object. In other words, there must be a lower level of living contagions on the decontaminated surfaces capable of reproducing or otherwise causing an infection after performance of the decontamination process than the level that existed on the surfaces immediately prior to performance of the decontamination process. For example, the exposed surfaces in the bathroom can be considered to be pathogen reduced if at least a 1 $\log_{10}$ reduction of such contagions on the surfaces remain infectious (i.e., no more than $\frac{1}{10}$th of the biologically-active contagions originally on the exposed surfaces remain active or infectious at a time when the decontamination process is completed) occurs. According to yet other embodiments, the surfaces can be considered pathogen reduced once at least a 3 $\log_{10}$ reduction (i.e., $\frac{1}{1,000}$th) of such contagions on the surfaces is achieved.

Although this exposure to the UVC light may not kill the contagions, the exposed contagions are unable to replicate as a result of the exposure to UVC light, thus promoting a lower level of replicating living contagions on the object after performance of the sterilization process than existed on the object prior to performance of the sterilization process. According to other embodiments, the object is required to possess a lower level of living or otherwise biologically-active contagions than a threshold quantity permitted under U.S. Food and Drug Administration requirements on objects dedicated for use in a sterile field such as in an operating room during a surgical procedure. According to other embodiments, the sterilization process kills or otherwise eliminates at least 99% of all living or otherwise biologically-active contagions present on the object immediately prior to performance of the sterilization process. According to yet other embodiments, achieving high-level disinfection of an object utilizing the disinfecting apparatus can involve deactivation of a suitable portion of the biologically-active contagions to achieve at least a 1 $\log_{10}$ reduction of such contagions on the object that remain infectious (i.e., no more than $\frac{1}{10}^{th}$ of the biologically-active contagions on the object remain active or infectious at a time when the decontamination process is completed). According to yet other embodiments, achieving a low to intermediate-level of disinfection of an object utilizing the disinfecting apparatus can involve deactivation of a suitable portion of the biologically-active contagions to achieve at least a 3 $\log_{10}$ reduction (i.e., $\frac{1}{1,000}^{th}$) 99.9% of such contagions on the object. According to yet other embodiments, achieving high-level disinfection of an object utilizing disinfecting apparatus can involve deactivation of a suitable portion of the biologically-active contagions to achieve at least a 6 $\log_{10}$ reduction (i.e., $1/1,000,000^{th}$) of such contagions on the object. Yet other embodiments requiring sterilization of the object can result in a complete and total absence of viable organisms on the object at a time when the decontamination process is completed.

Thus, although referred to as a "decontamination apparatus 10" herein for convenience, it is to be understood that the decontamination apparatus 10 subjects objects to a decontamination process that at least decontaminates, and can optionally disinfect or even optionally sterilize the objects by exposing the objects to UVC light or other suitable disinfectant or sterilizing agent. Once the decontamination process is complete, the objects are suitable for use in a sterile field such as an operating room during a surgical procedure or other healthcare-related practice.

Figure 2:
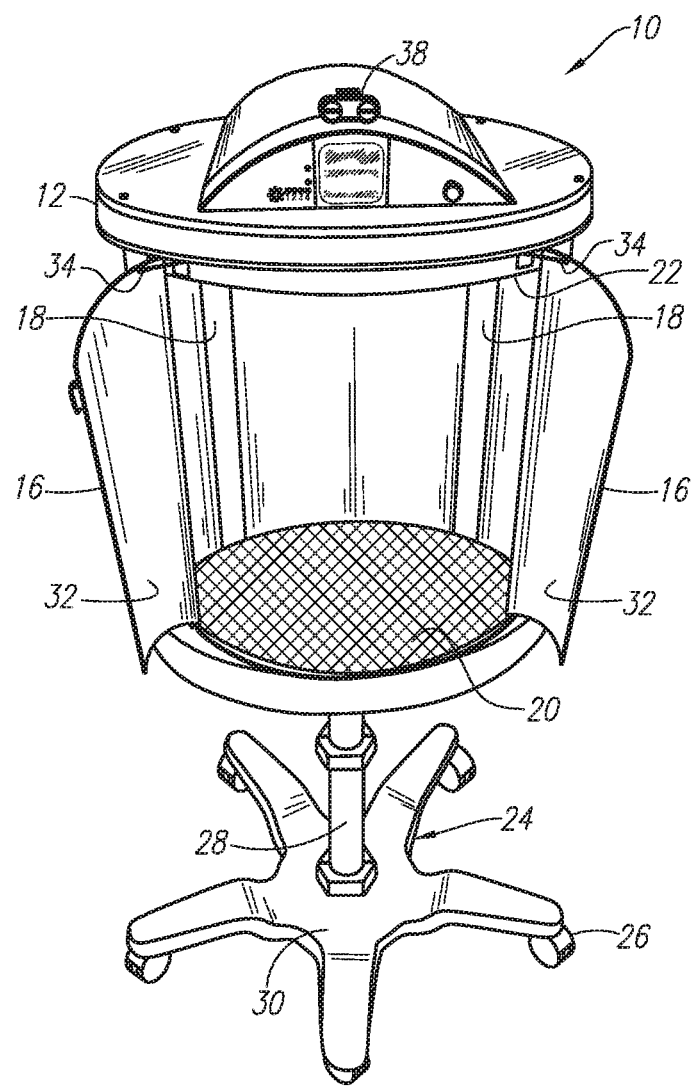
FIG. 2 is a perspective view of an illustrative embodiment of a decontamination apparatus, with a door open to receive objects to be rendered pathogen reduced.

Generally, the embodiment of the decontamination apparatus 10 interchangeably referred to herein as a disinfection apparatus 10, appearing in FIGS. 1 and 2 includes a housing 12 and at least one, and optionally a plurality of doors 16 that collectively enclose an interior space as a disinfecting chamber 14 in which objects to be decontaminated are to be placed. One or a plurality of sources, shown in the illustrated embodiment as one or more UVC light bulbs 18, direct a disinfecting agent in the form of UVC light toward the surface(s) of the object in the disinfecting chamber 14 to be rendered pathogen reduced.

Figure 3:
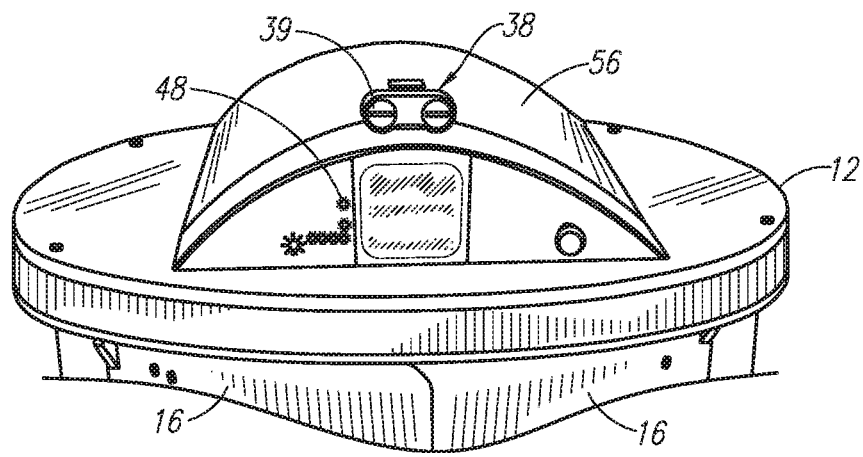
FIG. 3 is perspective view of an upper region of a housing provided to a decontamination apparatus, with a door restricting access to a storage compartment in a closed orientation.
Figure 4:
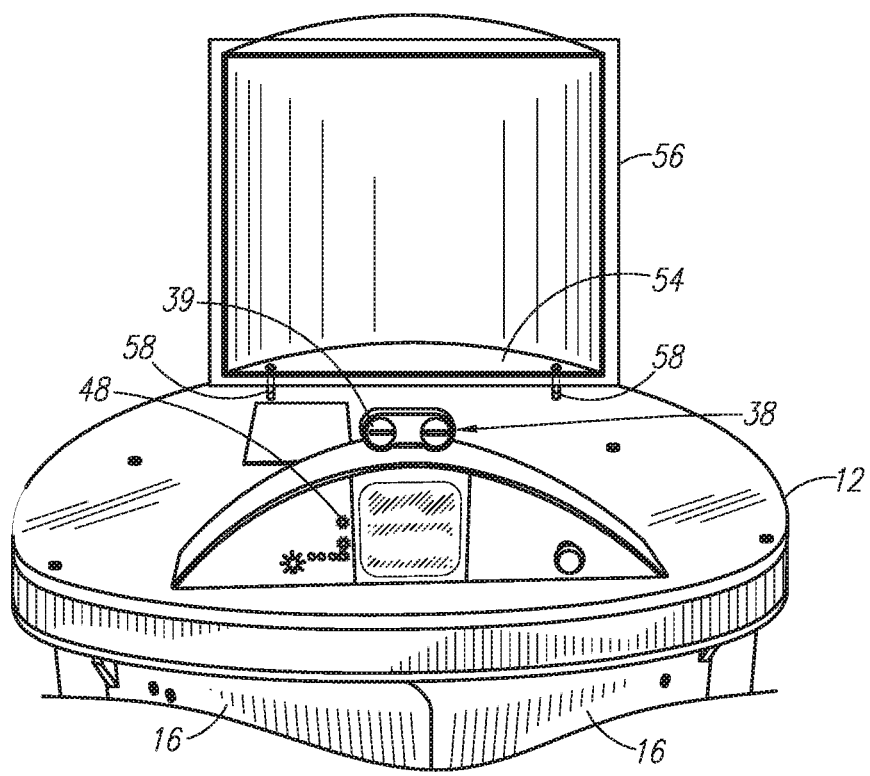
FIG. 4 is perspective view of an upper region of a housing provided to a decontamination apparatus, with a door restricting access to a storage compartment in an open orientation.

The housing 12 can be formed from a rigid plastic, metallic, other suitable material, or combinations thereof, and include at least one material that is opaque to UVC light to interfere with the emission of UVC light from the decontamination apparatus 10 into the ambient environment of the decontamination apparatus 10. Although shown in the drawings as being generally cylindrical in shape to accommodate at least one of a floor 20 and a ceiling 22 that rotates as described below, the housing 12 can also optionally be formed with an exterior and/or interior configured in any desired shape without departing from the scope of the present disclosure. As shown in FIGS. 3 and 4, the housing 12 can also include a storage compartment 54 that can be closed by a door 56 that is pivotally connected to the housing 12 by one or a plurality of hinges 58. The door 56 can optionally include a lock that secures the door 56 in the closed orientation to securely contain objects that may be commonly used with the decontamination apparatus 10 or that are to be transported with the portable embodiments of the decontamination apparatus 10.

A portable base 24 comprising a plurality of wheels 26, casters, etc. on which the housing 12 is mounted can optionally be provided to facilitate transportation of the decontamination apparatus 10 from one location to another. One or more upright pillars 28 extends upward from a carriage 30 supporting the wheels 26 of the portable base 24 to support the housing 12 at a convenient height above the ground. The wheels 26 can optionally be lockable, to interfere with movement of the decontamination apparatus 10 once positioned at a desired location. According to alternate embodiments, the decontamination apparatus 10 can include a stationary base that lacks wheels 26 for transportation, instead being provided with a carriage having a flat bottom that rests on the ground at a desired location. Such an embodiment of the decontamination apparatus 10 could be lifted to be transported from one location to another. Yet other embodiments of the decontamination apparatus 10 can lack the base 24 altogether. According to such embodiments, the housing 12 can be placed on a counter, desk, bench or other work surface. Like the embodiments with the stationary base, the housing 12 could be lifted to transport the decontamination apparatus 10 from one location to another. Alternately, the housing 12 could be "built in" to the wall or other structure at a location, establishing the decontamination apparatus 10 as a fixture at the healthcare facility.

The inward-facing surface 32 (FIG. 2) of at least one of the door 16 and the housing 12 that is exposed to the interior space of the decontamination chamber 14 can optionally be formed from, or otherwise provided with a liner of a UVC reflective material. The UVC reflective material has a reflectance that causes a substantial portion (e.g., at least 50%, at least 55%, at least 60%, at least 65%, at least 70%, at least 75%, at least 80%, at least 85%, at least 90%, and at least 95%) of UVC light emitted by the UVC bulbs 18 incident on the surface 32 to be reflected inward, into the decontamination chamber 14. Similarly, the inward-facing surface of the floor 20, and optionally the inward-facing surface of the ceiling 22 can be formed from, or otherwise provided with a liner of the UVC reflective material. Examples of the UVC reflective material include, but are not limited to polished aluminum. But regardless of the configuration of the disinfecting chamber 14, the disinfecting chamber 14 can optionally be sealed, optionally hermetically, to prevent air within the disinfecting chamber from venting into the ambient environment of the disinfecting apparatus 10. This seal can also prevent circulation of ambient air into the decontamination apparatus 10. Further, the decontamination apparatus 10 can optionally include, or be operatively connected to a vacuum source that is operable to optionally evacuate the disinfecting chamber 14.

A plurality of the UVC bulbs 18 can be distributed about the periphery of the inward-facing surface 32 of the housing 12 to emit UVC light generally toward a central region of the floor 20 as shown in FIG. 2. To minimize interference with UVC light emitted by other UVC bulbs 18, each of the UVC bulbs 18 can optionally be recessed into the lateral wall of the housing 12, to position an optional protective glass cover (which is UVC transparent) over the UVC bulbs 18 flush with an adjacent region of the inward-facing surface 32.

The housing 12 may be of any desired size. For example, in determining the size of the housing 12 is the volume of the disinfecting chamber 14. There are at least two competing interests in determining the size of the disinfecting chamber 14. First, the intensity of the UVC light emitted by the UVC light bulbs 18 deceases as distance from the source increases according to an inverse squared relationship, and the disinfecting factor of the UVC light is determined by the product of the intensity of this UVC light and the time of irradiation. Therefore, the larger the disinfecting chamber 14 is, the longer the decontamination process during which the UVC light is imparted on the objects in the disinfecting chamber 14 needs to be in order to reach an appropriate level of pathogen reduction. However, it is also desirable to have a disinfecting chamber 14 that is large enough to hold objects of various shapes and sizes, but smaller than would be required to allow an adult user to occupy the disinfecting chamber 14. For example, a computer keyboard requires a disinfecting chamber 14 that is approximately twenty inches tall whereas a pulse oximeter would require a disinfecting chamber that is only a few inches tall. Accordingly, it may be desirable in some embodiments to have a large disinfecting chamber 14 and in some embodiments to have a small disinfecting chamber 14. It should be noted that the size of the disinfecting chamber 14 is not intended to be a limiting parameter.

The floor 20 at the bottom of the disinfecting chamber 14 on which objects being decontaminated rest can optionally be stationary, and integrally formed as part of a monolithic structure along with the inward-facing surface 32 of the housing 12. According to alternate embodiments, the floor 20 can optionally be formed separate from the inward-facing surface 32 of the housing 12, and supported above a subfloor structure 27 of the housing 12 to pivot and/or rotate during decontamination processes about a central axis of a vertical mounting post 21 (FIG. 8) that extends between the floor and a floor motor 25. For example, the floor motor 25 can be operatively connected to a controller 40, described below, to be rotated or pivoted about the central axis of the mounting post 21 according to computer-executable instructions in a non-transitory computer-readable memory 42. As determined by the controller 40, the floor 20 can be rotated and/or pivoted at any desired angular velocity, such as angular velocities within a range from approximately one (1 rpm) revolution per minute to approximately ten (10 rpm) revolutions per minute.

Figure 5:
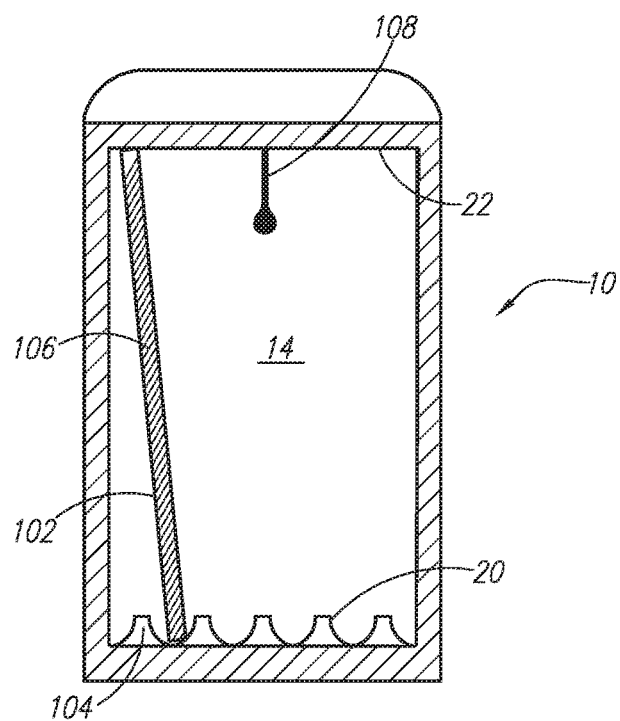
FIG. 5 is a partially cutaway view of the alternate embodiment of a decontamination apparatus shown in FIG. 7.
Figure 6:
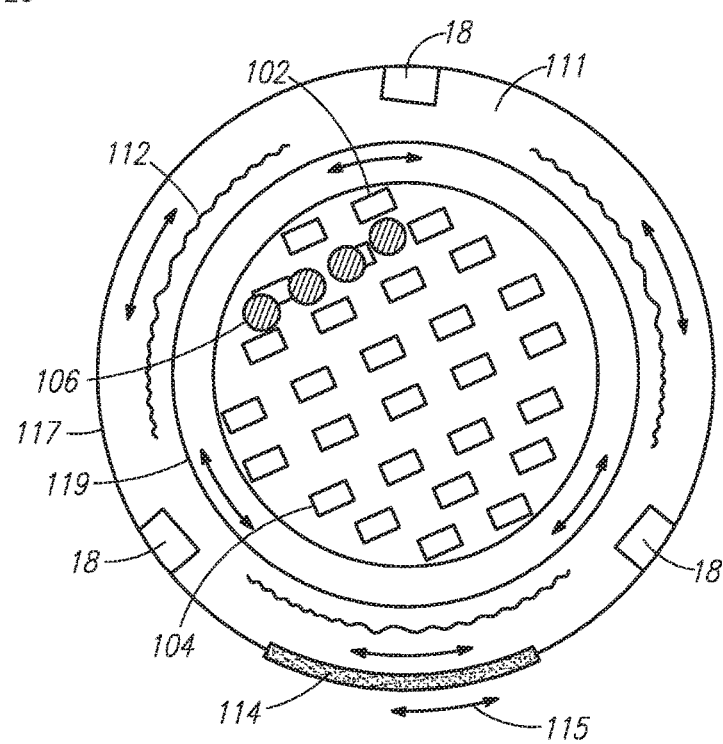
FIG. 6 is a partially cutaway view looking down onto the alternate embodiment of a decontamination apparatus shown in FIG. 7.

Although the floor 20 is described herein in detail as a generally planer structure, an alternate embodiment of the floor 20, shown in FIGS. 5 and 6, includes a plurality of upward-extending, pyramidal-shaped supports 104 projecting to an elevation within the disinfection chamber 14 vertically above a lower region of the floor 20. The upper surfaces of the supports 104 serve to limit the surface area of the floor 20 in contact with the object placed in the disinfecting chamber 14 because such contact areas could potentially inhibit UVC light from reaching the object to achieve the desired level of pathogen reduction. As shown in FIG. 5, the supports 104 have a profile that is somewhat frusto-conical when viewed from the side, with a rising surface truncated to form a planar top surface. According to an alternate embodiment shown in FIG. 8, the supports 104 can extend upward to an apex formed as a substantially pointed tip 105, thus having a profile appearance when viewed from the perspective of FIG. 8 of an upside down V shape. For any of the embodiments, including those with a substantially planar floor 20 such as that shown in FIG. 9, a substantially planar substrate 107 formed from a material that is substantially-transparent to UVC light, transmitting most of the UVC light reflected or transmitted upward from below without significant attenuation thereof, can optionally be overlaid on top of the floor 20 to help separate the object thereon from the floor 20. An illustrative example of a suitable material for the substrate 107 that is substantially transparent to UVC light is a half (0.5 in.) inch thick sheet of a fluorinated ethylene propylene ("FEP") polymeric material, although any suitably-transparent material can be used. The FEP polymeric material can optionally also be utilized in the construction of the floor 20 for alternate embodiments. In some embodiments, the floor 20 may support (e.g., in the in the troughs between the pyramidal shapes 104), overlay, or otherwise be positioned near optional additional UVC light bulbs, thereby increasing the likelihood the object receives UVC light at or near points of contact with the floor 20. In other embodiments the floor 104 may be constructed of UVC light sources disposed within quartz tubes so that even at points of contact with the object to be rendered pathogen reduced, the UVC light is imparted on all externally-exposed surfaces of the object. However, in embodiments where UVC light sources themselves act as a floor 20, the light sources may be subject to breaking if a heavy object is placed in the disinfecting chamber 14 or an object is dropped in to the disinfecting chamber 14. In these cases, it may be desirable to reinforce the UVC light sources. Any materials used to reinforce the UVC light sources should be substantially transparent to UVC light to permit transmission of a substantial portion (e.g., at least 60%, or at least 80%, or at least 90%, or at least 95%) of the UV light emitted. One illustrative example of such a material is quartz. Another material that is substantially-transparent and can be used to reinforce the UVC light bulbs is polypropylene. In still other embodiments, rather than resting on the pyramidal shapes 104 protruding from the floor 20, an object may rest in a basket, for example, a wire-frame or mesh basket optionally formed of quartz. As shown in FIG. 1, a substantially-planar mesh support (represented by the cross hatching on the floor 20 in FIG. 1) formed from crossing, interwoven, or other matrix of strands formed from a metal wire (which is optically opaque to UVC light), a quartz material (which is substantially transparent to UVC light), etc. can optionally be placed on the floor to elevate the object from the surface of the floor 20, which can optionally include a UVC reflective material that reflects the UVC light upward, toward the object. In such embodiments, UVC light emitted from UVC light bulbs 18 and reflected by the floor 20 can pass through the openings in the mesh to the object, while the small diameter of the metal wire, for example, forming the mesh limits the contact areas of the object that could potentially be at least partially shielded from UVC light by the mesh. According to other embodiments, the floor 20 itself can optionally be formed of the FEP polymeric material, fused silica or quartz, for example, and one or more UVC light bulbs 18 arranged vertically beneath the floor 20, thereby separating the objects to be disinfected from the UVC light bulbs 18. For such embodiments, the floor 20 can be approximately three sixteenths (3/16 in.) of an inch thick to transmit approximately 80%-85% of the UVC light emitted by those UVC light bulbs 18.

Figure 8:
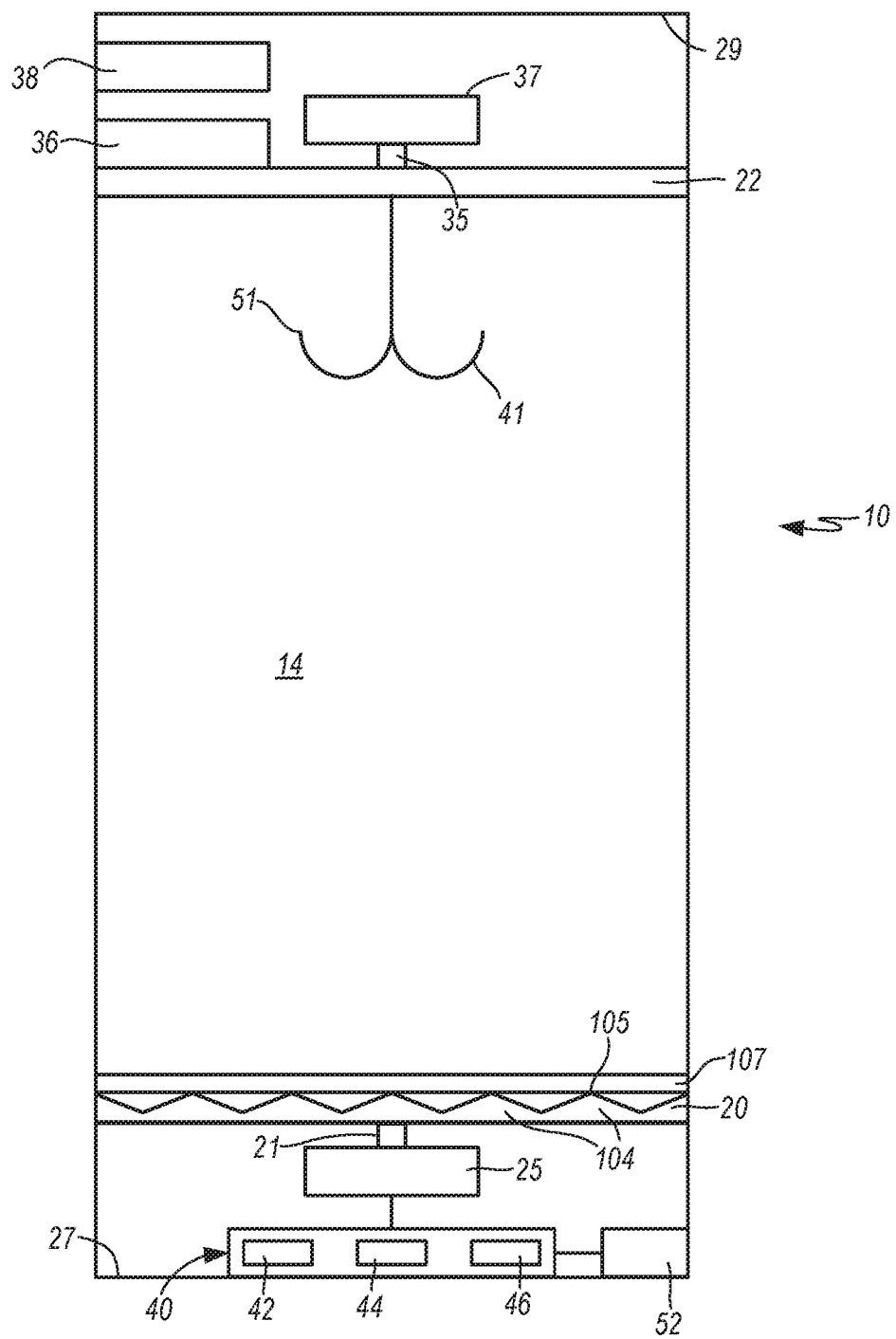
FIG. 8 is a schematic view of a decontamination apparatus including a floor with a plurality of upward-extending supports.
Figure 9:
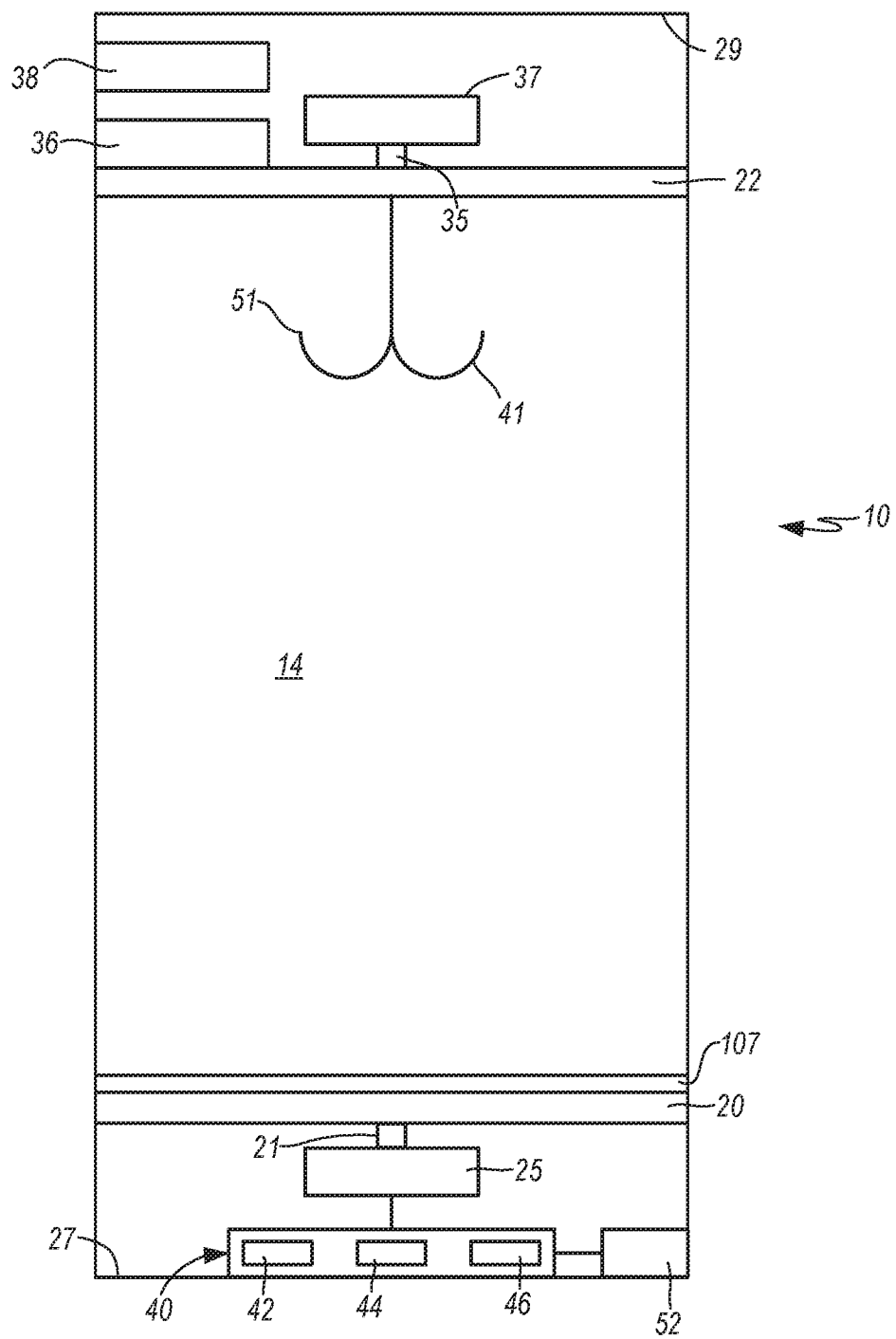
FIG. 9 is a schematic view of a decontamination apparatus including a planar floor with an overlaid substrate formed from a material that is substantially transparent to UVC light.

Similarly, the ceiling 22 defining the top of the disinfecting chamber 14 can optionally be stationary, and integrally formed as part of a monolithic structure along with the inward-facing surface 32 of the housing 12. According to alternate embodiments, the ceiling 22 can optionally be formed separate from the inward-facing surface 32 of the housing 12, and suspended from a superstructure 29 of the housing 12 above the ceiling 22 to pivot and/or rotate during decontamination processes about a central axis of a vertical mounting post 35, as shown in FIG. 8, that extends between the ceiling 22 and a ceiling motor 37. For example, the ceiling motor 37 can be operatively connected to a controller 40, described below, to be rotated or pivoted about the central axis of the mounting post 35 according to computer-executable instructions in the non-transitory computer-readable memory 42. As determined by the controller 40, the ceiling 22 can be rotated and/or pivoted at any desired angular velocity, such as angular velocities within a range from approximately one (1 rpm) revolution per minute to approximately ten (10 rpm) revolutions per minute. According to alternate embodiments, the ceiling motor 37 can optionally be operatively connected to cause rotation of the hook 41 instead of the ceiling 22, thereby causing rotation of the hook 21 within the disinfection chamber during a decontamination process relative to the stationary ceiling 22.

At least one hook 41, and optionally a plurality of hooks 41 or other suitable structure(s) from which objects being subjected to a decontamination process can be suspended above the floor 20 within the disinfecting chamber 14 can be coupled to the ceiling 22. The hook 41 can optionally be removable from, and re-attachable to the ceiling 22 by hand, without the use of a tool conferring a mechanical advantage. The hook 41 can optionally be formed of quartz or another material substantially transparent to UVC light, and can hang from the ceiling 22. The hook 41 can be useful to support objects with cords, such as pulse oximeters, so that the cord may dangle freely in the disinfecting chamber 14 and be exposed to the UVC light. In contrast, if the object with a cord was simply placed in the disinfecting chamber 102, the cord may "bunch" on the floor 20, possibly leaving contact points unexposed to UVC light.

According to alternate embodiments, the hook 41 may itself support its own UVC light bulb such as a UVC LED or similar compact UVC light source. In such embodiments, the inside of the object suspended from the hook 41 may also be exposed to the UVC light and rendered pathogen reduced. An illustrative example of such an object is a pulse oximeter. The aperture for a finger of the pulse oximeter may be clamped onto the end 51 of a hook 41 provided with a UVC LED that emits UVC light from the end 51 of the hook 41 to render the interior of the pulse oximeter pathogen reduced. According to other embodiments, rather than attaching the pulse oximeter or like object to the hook 41, the object may be similarly clamped to a tube or pyramidal shape 104 of the floor 20.

The disinfecting chamber 14 can also optionally include a wall 106 (FIGS. 5 and 6) or other suitable structure for leaning objects against. Since the wall 106 represents a large contact point with the object, in many embodiments the wall 106 is also made of a material that is substantially-transparent to UVC light. For example, the wall 104 could be made of tubes of quartz aligned next to each other.

The door(s) 16 can be mechanized to be opened and/or closed automatically, without physical contact with a human hand. For the embodiment shown in FIGS. 1 and 2, a plurality of opposed, double doors 16 cooperate to selectively close the entrance into the disinfecting chamber 14. A pushrod 34 extends between each door 16 and an actuator such as a door motor 36 (FIG. 8), which is operatively connected to a controller 40 that is operable to control opening and closing of the doors 16. Activation of the door motor 36 in a first direction according to instructions from the controller 40 extends the pushrods 34 outward from the housing 12, thereby urging the doors 16 open. Activation of the door motor 36 in a second direction, opposite the first direction, according to instructions from the controller 40 retracts the pushrods 34 into the housing 12, thereby urging the doors 16 closed.

To allow a user to control the opening and/or closing of the doors 16 without physically making contact with the doors 16, a vision system 38 including a photo eye, proximity sensor, or any suitable sensor 39 (FIGS. 3 and 4) that is operable to sense a user's hand in close proximity to the that can sense movement of an object near the housing 12 is operatively connected to the controller 40. Computer executable instructions stored in a non-transitory memory 42 in communication with a computer processor 44 provided to the controller 40 define a control routine based on signals transmitted by the vision system indicative of movement sensed by the sensor 39. When such instructions are executed by the computer processor 44, the computer processor 44 transmits a control signal to cause operation of the door 36 motor in a suitable direction to manipulate the position of the door(s) 16 without requiring physical contact between the user and the decontamination apparatus 10.

For example, a user can wave a hand in front of the sensor 39, and such sensed movement is converted into a signal transmitted by the vision system 38 to be received and interpreted by the computer processor 44 of the controller 40. In response to receiving such a signal, the computer processor 44 executes door-controlling instructions stored in the memory 42 to determine whether the doors 16 are open or closed. If the doors 16 are closed, the computer processor 44 transmits a signal that causes operation of the door motor 36 to open the doors 16. Conversely, if the doors 16 are open, the computer processor 44 transmits a signal that causes operation of the door motor 36 in a manner to close the doors 16 in response to the user waving a hand in front of the vision system 38. The computer processor 44, based on instructions in the memory 42, can also optionally automatically begin a decontamination process once the doors 16 are fully closed, or the computer processor 44 can commence the decontamination process in response to another hand wave or other suitable gesture being sensed by the vision system 38.

The gestures that control various operational aspects of the decontamination apparatus 10 are described as hand waves, but any gesture, movement, or other triggering event can be sensed to control the decontamination apparatus 10 in a touchless manner.

Figure 7:
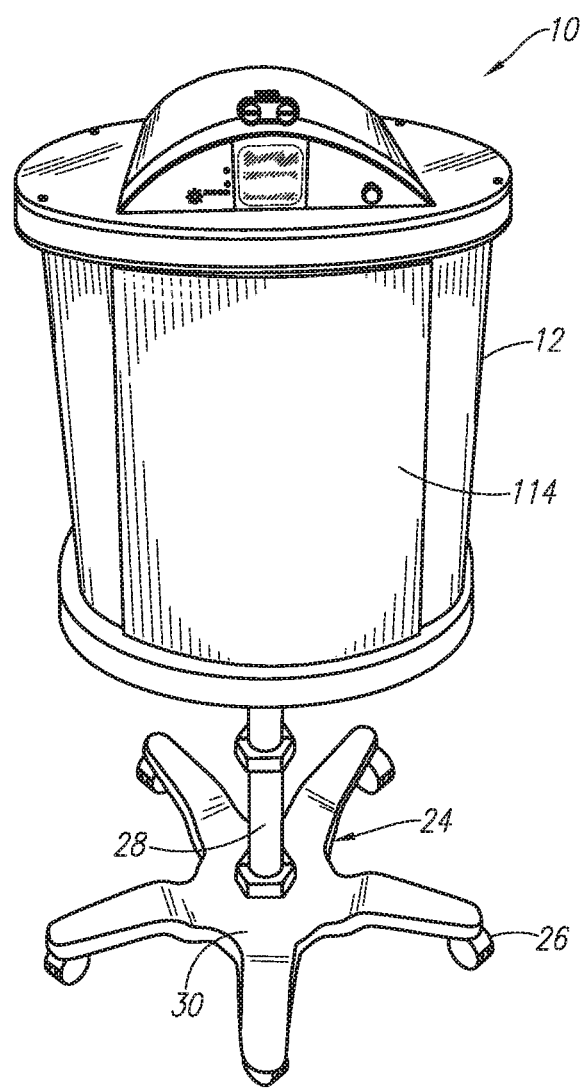
FIG. 7 is a perspective view of an illustrative embodiment of a decontamination apparatus, with a door closed during performance of a decontamination process.

Although the doors 16 are described above as opposing, hinged doors that close in directions toward the opposite door 16, the present disclosure is not limited to such a door configuration. For example, an alternate embodiment of a door 114 is shown provided to the embodiment of the decontamination apparatus 10 in FIG. 7. Rather than swing open similar to the doors 16 described above, the door 114 of the present embodiment slides between open and closed positions in the directions indicated by arrow 115 appearing in FIG. 6. The vision system 38, a proximity sensor positioned adjacent to the door 114, and/or any other suitable sensor can sense an object to be disinfected approaching, and being brought within close proximity to the door 114 to be placed inside the disinfecting chamber 14. The vision system 38 or other suitable sensor may also detect when the user's hand is removed from the disinfecting chamber 14. Upon detecting removal of the user's hand, the controller 40 automatically adjusts the position of the door 114 to the closed position.

An optional shield 112 formed as a panel of a material that is opaque to UVC light can optionally be arranged within a space 111 between an exterior shell 117 of the housing 12 and an interior liner 119 that defines the disinfection chamber 14 and includes the UVC reflective material, as shown in FIG. 6. The computer processor 44 (FIG. 8) of the controller 40 can execute instructions stored in the memory 42 to adjust the position of the shield 112 based on whether the door 114 is closed or in a partial or fully open state as an additional measure to interfere with UVC light emitted by the UVC light bulbs 18 from escaping the decontamination apparatus 10. For example, when the vision system 38 detects a gesture instructing the controller 40 to open the door 114, before the controller 40 begins to open the door 114 the controller 40 can adjust a position of the shields 112, one for each UVC light bulb 18, to be positioned in front of its respective UVC light bulb 18. With the shields 112 in place, the controller 40 can commence operation of the door motor 36 to open the door 114. Once the door 114 is returned to the fully-closed position, the controller 40 can again adjust the position of the shields 112 to allow emission of the UVC light emitted by the UVC light bulbs 18 into the disinfecting chamber 14.

When such a sensor recognize an object has been brought into close proximity with the door 114 to be placed in the disinfecting chamber the door 114, and optionally shield parts 112, rotate such that the disinfecting chamber 102 is exposed to a user placing an object in the disinfecting chamber 102. To prevent irradiation of a user or extraneous objects, the shield parts 112 rotate to cover each of the UVC light sources 110. But again, according to alternate embodiments, UVC light sources 110 that are adjustable instead of installed at a fixed location can optionally move behind the shields 112. However, for the sake of brevity, the shield parts 112 are illustrated as being adjustable depending on the state of the door 114. Sensors can also optionally detect when a user's hand is removed from the disinfecting chamber 102 after depositing the object to be disinfected.

The controller 40 can also optionally include a timer component 46, as shown in FIG. 8. The timer component 46 is shown as its own structure, separate from the computer processor 44, but the timer component 46 can optionally be integrated as a portion of the computer processor 44, executing computer-executable instructions stored in the memory 42 to perform the various timing functions described herein. Regardless of its configuration, the timer component 46 transmits a signal indicating that a predetermined period of time has expired. For example, in response to the vision system 38 sensing a gesture to close the doors 16 and initiate a decontamination process, the timer component 46 can be initialized to the desired length of the decontamination process. This desired length of time can optionally be programmable by users and/or administrators with managerial privileges, or can be pre-programmed as a default value stored in the memory 42. Regardless of how the desired length of time is established, once the timer component 46 determines this length of time has elapsed following initiation of a decontamination process, the timer component 46 transmits a signal notifying the computer processor 44 that the decontamination process is complete, and the UVC light bulbs 18 can be deactivated. According to alternate embodiments, the UVC light bulbs 18 can optionally be operated at a lower, but still active (e.g., the UVC light bulbs 18 remain on, as opposed to be switched off) power level than the power level at which the UVC light bulbs 18 were operating during the decontamination process to maintain the pathogen-reduced state of the objects in the disinfection chamber 14. According to yet other embodiments, the UVC bulbs 18 can be occasionally altered between on and off states following completion of the decontamination process until a time when the objects are removed from the disinfection chamber 18.

Once the decontamination process has been completed, the decontamination apparatus 10 can issue a visible, audible or other suitable indication that the decontamination process has been completed. For example, the decontamination apparatus 10 can include a light-emitting device, display device, or other selectively-operated indicator that, when observed, conveys information about the status of the decontamination process. For the illustrative embodiment in FIGS. 3 and 4, a multi-colored light-emitting diode ("LED") 48 can be illuminated to emit different colors of light based on the status of the decontamination apparatus 10. The LED 48 can emit green light to indicate that objects within the disinfection chamber 14 have been subjected to a decontamination process that was performed to completion (e.g., the UVC light bulbs 18 remained active for the duration of the predetermined period of time as determined by the timer component 46). The LED 48 can emit red light to indicate that objects within the disinfection chamber 14 have been subjected to a decontamination process, but the decontamination process was prematurely interrupted before it was completed (e.g., the UVC light bulbs 18 were deactivated as a result of a command to open the doors 16, an attempt to manually open the doors 16, manual entry of a cancel command, unexpected loss of electric power, etc., prior to expiration of the predetermined period of time as determined by the timer component 46). The LED 48 can emit yellow light to indicate that objects within the disinfection chamber 14 are currently undergoing an active decontamination process has not yet been completed (e.g., the UVC light bulbs 18 have remained active, uninterrupted, but the predetermined period of time as determined by the timer component 46 has not yet expired). The above examples are meant to be illustrative. Any suitable indicator, whether visible (e.g., flashing LED 48, etc.), audible (e.g., beeping sound from a speaker, etc.) or any combination thereof, can be used to convey status information about the decontamination apparatus 10 and its operation.

As noted above, the decontamination process can be prematurely interrupted, meaning that the objects within the disinfection chamber 14 may not have been exposed to the required dose of UVC light to achieve the desired level of decontamination. Rather than simply allowing the decontamination process terminate prematurely and indicating this status, the controller 40 can optionally be configured to automatically (e.g., without manual user intervention) resume the prematurely-interrupted decontamination process from the point at which it was prematurely interrupted if the interruption is determined by the controller 40 to be momentary (e.g., shorter than five (5) minutes or other predetermined period of time programmed into the controller 40), and/or optionally automatically restart the decontamination process from the beginning if the interruption is determined by the controller 40 to be lengthy (e.g., greater than 5 minutes or other predetermined period of time programmed into the controller 40). The status of the decontamination apparatus 10 indicated by the LED 48 or other suitable indicator can reflect the current status. Thus, if the decontamination process was prematurely interrupted, restarted and completed, the status indicator will indicate that the decontamination process has been successfully completed.

Alternate embodiments of the decontamination apparatus can optionally include a network-communication port 52 that is operatively connected to the controller 40 to facilitate network communications between the controller 40 and a remote computer. For example, the network-communication port 52 can include a wireless communication antenna that is configured to communicate over short range (e.g., Bluetooth, etc.) local wireless networks, over WiFi wireless networks compliant with the 802.11 and/or other standards promulgated by The Institute of Electrical and Electronics Engineers. According to alternate embodiments, the network-communication port 52 can include a wired connection component such as an Ethernet (e.g., RJ-45) jack, and the like. Status information available to the controller 40, including information about any of the operational aspects of the decontamination apparatus 10 described herein, can be transmitted over a private local area network ("LAN"), wide area network ("WAN"), or a combination thereof to a desired recipient. Such an intended recipient can be a cleaning administrator responsible for operation of the decontamination apparatus 10, or any other person to whom status reports should appropriately be sent.

Although UVC light bulbs 18 are described herein as examples of the decontaminating sources, alternate embodiments of the sterilizing or disinfecting agent sources can include, but are not limited to Xenon light sources or any other source of radiation that can be used to render objects materially disinfected are within the scope of the present disclosure. For instance, strobed Xenon light sources, with their operation timed to prevent operation during times when the doors 16 or the no-touch door 114 and/or shield 112 described herein are open. For any of the embodiments described herein not utilizing pulsed sources, operation of such sources during the disinfection process can optionally be limited to a period that minimizes the yellowing exhibited by surfaces exposed to the sources during disinfection.

In other embodiments, one or a plurality of UVC light bulbs 18 may be located at the top of the disinfecting chamber 14, adjacent to the ceiling 22. In such embodiments, the UVC light bulbs 18 may hang from the ceiling, or extend parallel to the ceiling 22. UVC light sources may also be embedded in the ceiling in a manner similar to that described with respect to the floor 104.

Although the embodiments described above include a disinfecting chamber 14 in which objects are to be placed, by hand, to be exposed to a disinfecting agent and rendered pathogen reduced, other embodiments include a disinfecting chamber 14 with a floor 20 that is located approximately at a level of a ground surface on which the decontamination apparatus 10 rests. Such a disinfecting chamber 14 can extend upwardly a suitable height to allow hospital furniture such as an IV stand on which an IV bag is, or has been suspended, to be rolled into the disinfecting chamber 14 without having to be elevated above more than a molding exposed while the doors 16 are open. Such embodiments may include a door that closes all the way to the ground surface on which the decontamination apparatus 10 rests, preventing the UVC light from exiting the disinfecting apparatus 10 during operation. In use, the IV stand or other wheeled object to be rendered materially disinfected can be rolled over a mat or otherwise wiped down with a disinfectant when the IV stand is rolled into or out of the disinfecting apparatus 10. An infusion pump or other object supported by the IV stand can optionally remain in place during operation of the disinfecting apparatus 10, also rendering the exposed surfaces of those objects materially disinfected. Such usage would not expose every single surface of the IV stand, infusion pump and/or other object to the UVC light. However, the exposed surfaces of those objects that operators will commonly come into contact with during typical usage are rendered materially disinfected.

Although adjusting the position of the object relative to the UVC light bulbs 18 is accomplished in the description above by rotating and/or pivoting the object through a pivotal or rotational floor 20, ceiling 22 and/or hook 41. However, alternate embodiments can achieve thorough exposure of the object to UVC light by rotating at least one, and optionally a plurality or all of the UVC light bulbs 18 about a stationary object in the disinfecting chamber 14.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus for rendering an object pathogen reduced, the apparatus comprising:
    a housing enclosing a disinfecting chamber in which the object is to be placed;
    an ultraviolet light source arranged to emit UVC light into the disinfecting chamber to be imparted on the object in the disinfecting chamber for deactivating at least a portion of a biologically-active contagion present on the object;
    a peripheral wall of the housing that extends about a portion of the disinfecting chamber and comprises an ultraviolet-reflective material so that the ultraviolet light impinging on the peripheral wall is reflected generally away from the peripheral wall and toward an interior of the disinfecting chamber;
    a floor that defines a bottom surface of the disinfecting chamber and supports the object within the disinfecting chamber, wherein the floor is formed separate from an inward-facing surface of the housing and is supported above a subfloor structure of the housing, wherein the floor includes a plurality of upward-extending, pyramidal-shaped supports projecting to an elevation within the disinfection chamber vertically above the floor;
    a substrate placed over the supports projecting vertically above the floor to be arranged between the object in the disinfecting chamber and the floor to separate the object from the floor, wherein the floor that defines the bottom surface of the disinfecting chamber comprises an ultraviolet-reflective surface that reflects the ultraviolet light impinging on the floor generally away from the floor toward an underside of the object resting on top of the substrate; and
    a rotation device operatively connected to the floor to rotate the floor supporting the object within the disinfecting chamber during a decontamination process.

2. The apparatus of claim 1, further comprising a controller that is configured to control operation of the ultraviolet light source to activate the ultraviolet light source as part of the decontamination process and cause the ultraviolet light source to remain active for a predetermined duration of the decontamination process.

3. The apparatus of claim 1, further comprising a door that is adjustable between open and closed orientations to selectively permit access to the disinfecting chamber and interfere with emission of the ultraviolet light from the disinfecting chamber into an ambient environment of the apparatus.

4. The apparatus of claim 2, wherein the rotation device is a motor.

5. The apparatus of claim 4, wherein the motor causes the floor to rotate around a central axis of a mounting post, wherein the mounting post extends between the floor and the motor.

6. The apparatus of claim 5, wherein the motor is operatively connected to the controller.

7. The apparatus of claim 2, wherein the controller is operatively connected to a computer-readable memory, wherein the computer-readable memory provides computer-executable instructions to the controller.

8. The apparatus of claim 7, wherein the computer-executable instructions comprise a desired angular velocity of the floor rotation.

9. The apparatus of claim 8, wherein the desired angular velocity ranges from one revolution per minute to ten revolutions per minute.

10. The apparatus of claim 1 further comprising a hanging device that extends downward from a ceiling of the disinfecting chamber from which the object can be hung.

11. The apparatus of claim 10, further comprising an operational connection between: (i) at least one of the ceiling and the hanging device, and (ii) a second rotation device to cause rotation of at least one of the ceiling and the hanging device during the decontamination process.

12. The apparatus of claim 1, wherein the ceiling comprises an ultraviolet-reflective surface that reflects the ultraviolet light impinging on the ceiling generally away from the ceiling toward an interior of the disinfecting chamber.

13. The apparatus of claim 2, wherein the controller is operatively connected to a network communication port to transmit status information relating to an operational status of the apparatus to a remotely-located computer via the network communication port.

14. The apparatus of claim 1, wherein the floor that defines the bottom surface of the disinfecting chamber comprises an ultraviolet-reflective surface that reflects the ultraviolet light impinging on the floor generally away from the floor toward the interior of the disinfecting chamber.

15. The apparatus of claim 1, wherein the substrate comprises a material that is substantially transparent to UVC light.

16. The apparatus of claim 15, wherein the material is a fluorinated ethylene propylene (FEP) polymeric material.

17. An apparatus for rendering an object pathogen reduced, the apparatus comprising:
   a housing enclosing a disinfecting chamber in which the object is to be placed;
   an ultraviolet light source arranged to emit UVC light into the disinfecting chamber to be imparted on the object in the disinfecting chamber for deactivating at least a portion of a biologically-active contagion present on the object;
   a peripheral wall of the housing that extends about a portion of the disinfecting chamber and comprises an ultraviolet-reflective material so that the ultraviolet light impinging on the peripheral wall is reflected generally away from the peripheral wall and toward an interior of the disinfecting chamber;
   a floor that defines a bottom surface of the disinfecting chamber and supports the object within the disinfecting chamber, wherein the floor comprises a plurality of upward-extending supports that extend upward into the disinfecting chamber from a lower region of the floor, such plurality of upward-extending supports being spaced apart from each other, and wherein the supports extend upward to an apex formed as a substantially pointed tip.

18. The apparatus of claim 17 further comprising a substrate positioned over the plurality of upward-extending supports in the disinfecting chamber.

19. The apparatus of claim 18, wherein the substrate is substantially transparent to UVC light.

20. The apparatus of claim 18, wherein the substrate is fluorinated ethylene propylene polymeric material.

* * * * *